United States Patent
Boamfa et al.

(10) Patent No.: US 10,268,031 B2
(45) Date of Patent: Apr. 23, 2019

(54) ILLUMINATION IN DIGITAL PATHOLOGY SCANNING

(71) Applicant: KONINKLIJKE PHILIPS N.V., Eindhoven (NL)

(72) Inventors: Marius Iosif Boamfa, Eindhoven (NL); Reinhold Wimberger-Friedl, Eindhoven (NL); Theodoor Bastiaan Johannes Haddeman, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 17 days.

(21) Appl. No.: 15/517,015

(22) PCT Filed: Mar. 7, 2016

(86) PCT No.: PCT/EP2016/054724
§ 371 (c)(1),
(2) Date: Apr. 5, 2017

(87) PCT Pub. No.: WO2016/146411
PCT Pub. Date: Sep. 22, 2016

(65) Prior Publication Data
US 2017/0299852 A1    Oct. 19, 2017

(30) Foreign Application Priority Data
Mar. 19, 2015    (EP) .................................. 15159793

(51) Int. Cl.
*G02B 3/00*    (2006.01)
*G01N 21/64*    (2006.01)
(Continued)

(52) U.S. Cl.
CPC ..... *G02B 21/0076* (2013.01); *G01N 21/6456* (2013.01); *G01N 21/6458* (2013.01);
(Continued)

(58) Field of Classification Search
CPC ............ G02B 21/0076; G02B 21/0032; G02B 21/0052; G02B 21/12; G01N 21/6458; G01N 2021/6471; G01N 2021/6478
See application file for complete search history.

(56) References Cited

U.S. PATENT DOCUMENTS 6,028,306 A    2/2000  Hayashi
7,715,001 B2 *  5/2010  Lundquist ................. G01J 3/02
                                                    356/244

(Continued)

FOREIGN PATENT DOCUMENTS

WO    2011080670 A1    7/2011
WO    2012159205 A1    11/2012
(Continued)

*Primary Examiner* — Christine S. Kim
(74) *Attorney, Agent, or Firm* — Sherry Womack Austin

(57) ABSTRACT

The present invention relates to digital pathology. In order provide enhanced use of available imaging radiation, a digital pathology scanner (10) is provided that comprises a radiation arrangement (12), a sample receiving device (14), an optics arrangement (16), and a sensor unit (18). The radiation arrangement comprises a source (20) that provides electromagnetic radiation (22) for radiating a sample received by the sample receiving device. Further, the optics arrangement comprises at least one of the group of a lens (24) and a filter (26) that are arranged between the sample receiving device and the sensor unit. The sensor unit is configured to provide image data of the radiated sample. Still further, a lens array arrangement (28) is provided that comprises at least one lens array (30) arranged between the source and the sample receiving device. The at least one lens array comprises a plurality of linear cylindrical lenses (32) that modulate the electromagnetic radiation from the source such that, in an object plane, a radiation distribution pattern (34) is generated with a plurality of first parts of intensified radiation and a plurality of second parts of weak radiation.

17 Claims, 3 Drawing Sheets

(51) Int. Cl.
　　　*G02B 21/00*　　　(2006.01)
　　　*G02B 21/08*　　　(2006.01)
　　　*G02B 21/12*　　　(2006.01)
　　　*G02B 21/16*　　　(2006.01)
　　　*G02B 21/36*　　　(2006.01)

(52) U.S. Cl.
　　　CPC ......... *G02B 3/005* (2013.01); *G02B 21/0032* (2013.01); *G02B 21/0052* (2013.01); *G02B 21/082* (2013.01); *G02B 21/12* (2013.01); *G02B 21/16* (2013.01); *G02B 21/367* (2013.01); *G01N 2021/6471* (2013.01); *G01N 2021/6478* (2013.01)

(56) References Cited

U.S. PATENT DOCUMENTS

| | | |
|---|---|---|
| 2002/0074493 A1 | 6/2002 | Hill |
| 2011/0228537 A1 | 9/2011 | Yoshimizu |
| 2014/0252200 A1 | 9/2014 | Garsha |
| 2014/0268319 A1 | 9/2014 | Gulari |
| 2014/0313516 A1 | 10/2014 | Uhl |

FOREIGN PATENT DOCUMENTS

| | | |
|---|---|---|
| WO | 2014000085 A1 | 1/2014 |
| WO | 2014013412 A1 | 1/2014 |
| WO | 2014188622 A1 | 11/2014 |

\* cited by examiner

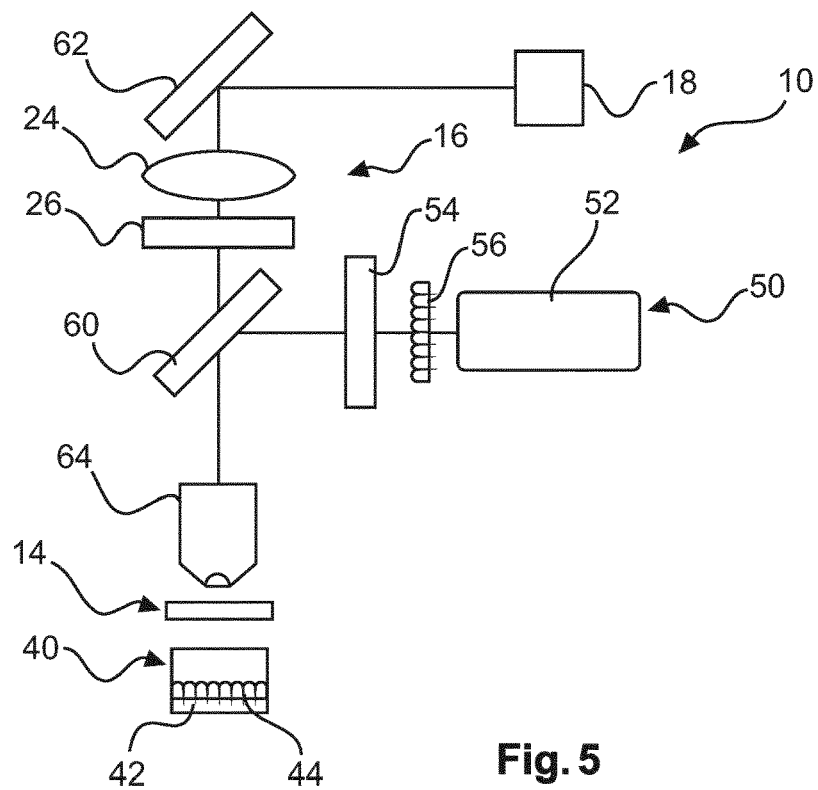
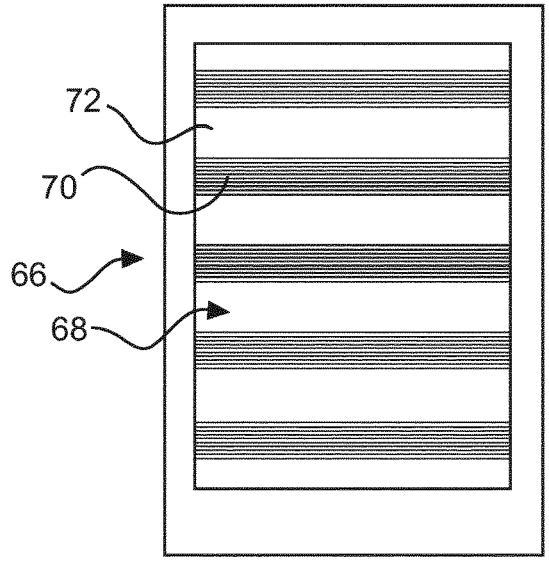
Fig. 6
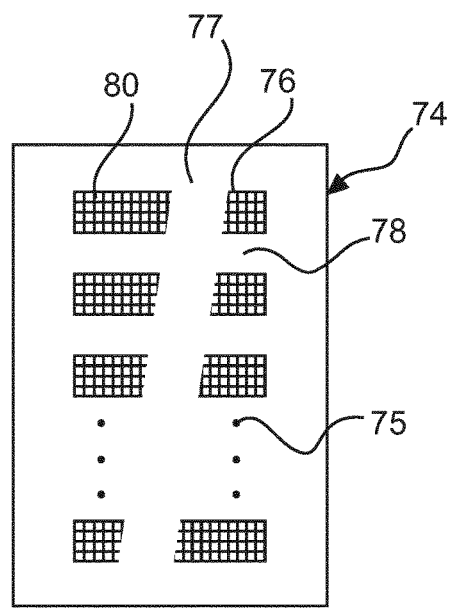
Fig. 7
Fig. 5

ILLUMINATION IN DIGITAL PATHOLOGY SCANNING

CROSS-REFERENCE TO PRIOR APPLICATIONS

This application is the U.S. National Phase application under 35 U.S.C. § 371 of International Application No. PCT/EP2016/054724, filed on Mar. 7, 2016, which claims the benefit of European Patent Application No. 15159793.7, filed on Mar. 19, 2015. These applications are hereby incorporated by reference herein.

FIELD OF THE INVENTION

The present invention relates to digital pathology, and relates in particular to a digital pathology scanner.

BACKGROUND OF THE INVENTION

In order to integrate pathology images in a clinical decision support system of, for example, a hospital, pathology slides are made available in digital form. Hence, this is referred to as digital pathology. Pathology slides are usually scanned by a digital pathology scanner provided for this purpose to make the images available for further inspection in a digital form. In order to be able to acquire the images, the pathology slide has to be illuminated. WO 2011/080670 A1 describes a sensor for microscopy in a digital scanner for digital pathology. It has been shown that the quality of the illumination is a demanding topic. For scanning, a low resolution scan for preview purposes may be provided and a high resolution scan may be provided for the actual image acquisition. The preview is provided for example to identify the area of interest. The high resolution scans are provided to scan the area of interest at high resolution with the speed that is mostly determined by the available light limitations. However, it has been shown that an efficient use of the available light from the light source is a central aspect for high scanning speed.

SUMMARY OF THE INVENTION

There may thus be a need to provide a digital pathology scanner with enhanced use of available imaging radiation.

The object of the present invention is solved by the subject-matter of the independent claim, wherein further embodiments are incorporated in the dependent claims.

According to the invention, a digital pathology scanner is provided that comprises a radiation arrangement, a sample receiving device, an optics arrangement, and a sensor unit. The radiation arrangement comprises a source that provides electromagnetic radiation for radiating a sample received by the sample receiving device. The optics arrangement comprises at least one of the group of a lens and a filter, which are arranged between the sample receiving device and the sensor unit. The sensor unit is configured to provide image data of the radiated sample. A lens array arrangement is provided comprising at least one lens array arranged between the source and the sample receiving device. The at least one lens array comprises a plurality of linear cylindrical lenses that modulate the electromagnetic radiation from the source such that, in an object plane, a radiation distribution pattern is generated with a plurality of first parts of intensified radiation and a plurality of second parts of weak radiation.

The provision of the above-described lens array arrangement achieves a concentration of the provided radiation and thus makes efficient use of the provided radiation for illumination purposes. In the intensified radiation parts, more radiation, e.g. light, is provided than without the use of the lens array arrangement. Hence, a concentration of light (illumination) in form of the provided intensified radiation parts allows a more efficient use of the light (illumination) and thus supports high scanning speeds.

In an example, two or more, e.g. four, five, six, seven, eight, nine, ten or more, lens arrays are provided in the scanner.

According to an example, the linear cylindrical lenses are arranged adjacent to each other to provide a continuous modulation of the electromagnetic radiation from the source. This allows an optimized use of all the radiation, e.g. all the light provided by the source.

According to an example, the radiation arrangement comprises an illumination unit with a light source. The lens array arrangement comprises an illumination lens array that is arranged between the light source and the sample receiving device and that modulates light from the light source such that an illumination distribution pattern is generated with a plurality of first parts of intensified illumination and a plurality of second parts of weak illumination.

This provides that illumination light can be provided to the sample for scanning the sample, e.g. in a transmissive way.

According to an example, the optics arrangement is configured for transmissive illumination mode for bright field mode scanning, in which light from the illumination unit is transmitted directly towards the sensor unit.

According to an example, the radiation arrangement comprises a fluorescence excitation unit with an excitation light source and an excitation filter in front of the excitation light source. The lens array arrangement comprises an excitation lens array that is arranged between the excitation light source and the sample receiving device and that modulates excitation light from the excitation light source such that an excitation distribution pattern is generated with a plurality of first parts of intensified excitation light and a plurality of second parts of weak excitation light.

Hence, the sample can also be imaged in terms of providing fluorescent image information.

According to an example, the optics arrangement is configured for a reflective illumination mode for fluorescence mode scanning, in which light from the fluorescence excitation unit is transmitted towards the sample, and in which generated fluorescence radiation is then transmitted towards the sensor unit.

In an example, both modes are provided, i.e. transmissive illumination mode and fluorescence mode, by providing the illumination unit with the illumination lens array and the fluorescence excitation unit with the excitation lens array.

According to an example, the sensor unit comprises a sensor with a sensor pattern of a plurality of first parts of linear photo-active areas and a plurality of second parts of photo-inactive areas in between. The number of the plurality of linear cylindrical lenses matches the number of the plurality of linear photo-active areas.

This allows the efficient use of the light provided by the light source and hence efficiency is increased significantly and thus enables faster scanning According to an example, one linear photo-active area comprises one or multiple pixel lines, for example, one linear photo-active area could comprise four pixel lines. These pixel lines of a linear photo-active area work in time delay and integration mode (TDI mode), also referred to as time delay and integration scanning which can enhance sensitivity.

According to an example, the sensor pattern is provided with a ratio of the photo-active areas to the photo-inactive areas of smaller than 1:1, for example having a ratio of 4:13.

According to an example, the radiation distribution pattern or the illumination distribution pattern or the excitation distribution pattern in the object plane is corresponding to the sensor pattern.

In another example, two or more of the radiation distribution pattern, the illumination distribution pattern, and the excitation distribution pattern in the object plane are corresponding to the sensor pattern.

According to an aspect, a lens array is provided in order to modulate the electromagnetic radiation, i.e. the light, already in the object plane for providing intensified regions in the object plane that allow, at least referring to these regions, a more efficient use of the light and thus allows faster scanning speeds. The provision of the lens array and the distribution of the intensified parts in the object plane can match with a respective pattern of sensor segments, which provides the respective image data.

These and other aspects of the present invention will become apparent from and be elucidated with reference to the embodiments described hereinafter.

BRIEF DESCRIPTION OF THE DRAWINGS

Exemplary embodiments of the invention will be described in the following with reference to the following drawings:

FIG. 5 shows a setup of a further example of a digital pathology scanner with further options.

FIG. 6 shows a light distribution pattern across an object plane of the scanner of FIG. 1.

FIG. 7 shows an example of a sensor unit used in the scanner of FIG. 1.

DETAILED DESCRIPTION OF EMBODIMENTS

Figure 1:
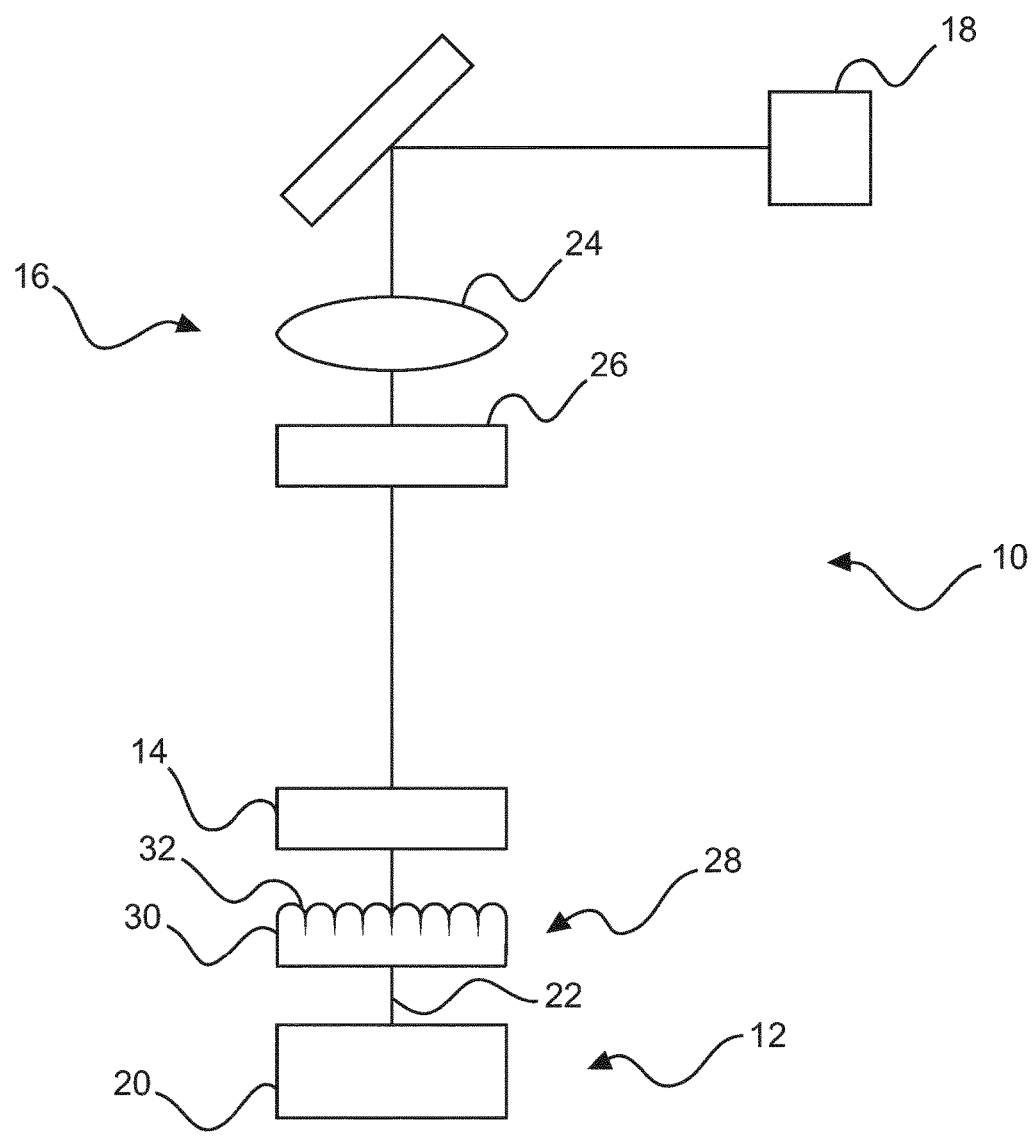
FIG. 1 shows a schematic setup of an example of a digital pathology scanner.

FIG. 1 illustrates a diagram of a digital pathology scanner 10. It is noted that FIG. 1 also illustrates options that are provided as an example, but that are not mandatory for the below described digital pathology scanner 10.

The digital pathology scanner 10 comprises a radiation arrangement 12, a sample receiving device 14 and an optics arrangement 16. Still further, a sensor unit 18 is provided.

The radiation arrangement 12 comprises a source 20 that provides electromagnetic radiation 22 for radiating a sample received by the sample receiving device 14. The optics arrangement 16 comprises at least one of the group of a lens 24 and a filter 26, which are arranged between the sample receiving device 14 and the sensor unit 18. The sensor unit 18 is configured to provide image data of the radiated sample. Further, a lens array arrangement 28 is provided comprising at least one lens array 30 arranged between the source 20 and the sample receiving device 14. The at least one lens array 30 comprises a plurality of linear cylindrical lenses 32 that modulate the electromagnetic radiation 22 from the source 20 such that, in an object plane (not further indicated), i.e. the plane in which the object is arranged, a radiation distribution pattern (see also below) is generated with a plurality of first parts of intensified radiation and a plurality of second parts of weak radiation.

The lens array arrangement provides a concentration of the radiation, i.e. light used for scanning, to particular areas and allows an improved scanning in these areas. This increases efficiency, and enables, for example, a faster scanning It is noted that in the following, also more detailed examples for the arrangement of the source 20 are provided.

Figure 2:
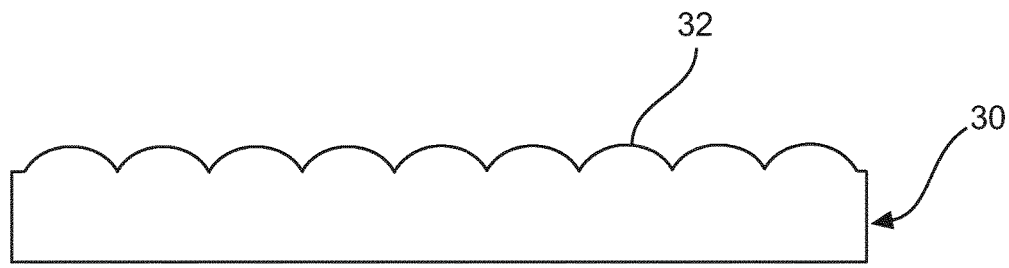
FIG. 2 shows a cross-section of a lens array used in the scanner of FIG. 1.

In FIG. 2, a detailed cross-section of the at least one lens array 30 is provided. The plurality of linear cylindrical lenses 32 is shown.

Figure 3:
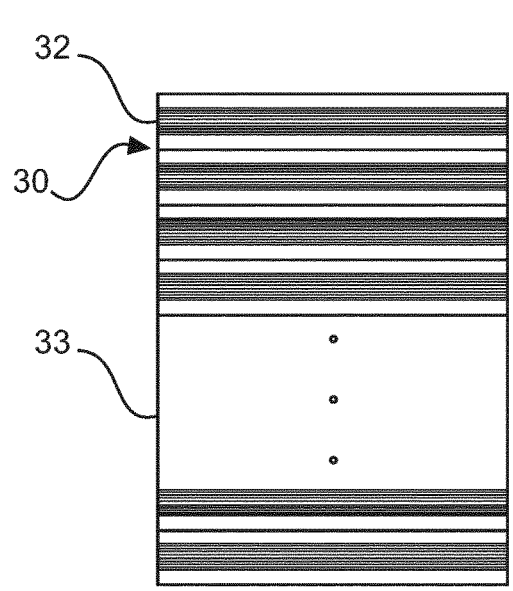
FIG. 3 shows a top view of the lens array of FIG. 2.

In FIG. 3, a top view of the at least one lens array 30 is indicated. An empty part 33 indicates that the lens array may have further lines of the linear cylindrical lenses 32 and can vary in size and also in proportion, i.e. the lens array 30 can have more or less lines of the linear cylindrical lenses 32, and the linear cylindrical lenses 32 can have a longer or shorter extension in the linear direction.

Figure 4:
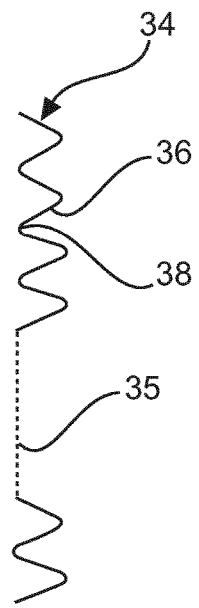
FIG. 4 shows a light distribution pattern caused by the lens array of FIG. 2.

In FIG. 4, shown next to FIG. 3, an intensity distribution pattern 34 is shown that results from the plurality of linear cylindrical lenses 32. As can be seen, an alternating pattern of the first parts of intensified radiation, indicated with reference numeral 36, is provided in addition to the plurality of second parts of weak radiation, as indicated with reference numeral 38. A dotted line 35 indicates that the graph can vary further in dependency of the lens array. The lens array arrangement 28 provides an alteration of light distribution in the object plane, which can also be referred to as sample plane.

The electromagnetic radiation can be provided for example as visible light or as invisible light, such as infrared light or ultraviolet light.

The term "to modulate" can also be referred to as to focus the radiation.

The term "digital pathology" relates to providing information from samples or probes in form of digital slides. The terms "sample" or "probe" relate to examples that are provided to be imaged. For example, the probe is a stained tissue provided in form of a slide. An image is taken from a slice of tissue or fluid or other sample as a probe, and the image is then provided to an image management system in digital form. The acquired images are provided as pathology images (or pathology slides) similar to what can be provided by microscopy. Hence, the term digital microscopy, or virtual microscopy, can also be used. The digital slides allow viewing, analyzing and managing the data in a computer environment. The term "digital pathology scanner" relates to a device provided for scanning probes to generate image data as digital slides. A probe can be provided, for example as a prepared or pre-treated probe, in order to be illuminated and scanned to acquire the image data in digital form. The scanner may be provided to be suitable for a facilitated acquisition of a large number of slides.

The term "radiation arrangement" relates to parts of the scanner that provide the light (visible or invisible to the human eye) for the actual scanning process, e.g. the pre-scan procedure or the main scan procedure. The "radiation arrangement" can be provided as an "illumination unit" to illuminate the probe to be able to detect respective image information by the sensor unit acting as imaging unit. The term "illumination unit" relates to a unit or component for generating light for further purposes.

The term "object plane" relates to a plane, in which a sample is arranged during the scanning procedure. The "object plane" is also referred to as sample plane. The object plane is thus different from an imaging plane, since the sensor unit is arranged not in the same plane as the object, i.e. the sample or probe.

The "sample receiving device" relates to a provision to temporarily hold a sample for the scanning procedure. In an example, an insert or receptacle for receiving a sample holder is provided. The sample holder may be provided as a glass plate (or two glass plates) supporting the sample to be scanned that may also be temporarily fixed to the sample holder. In another example, a designated space is provided to arrange the sample for the imaging purpose, e.g. as a sample receiving space.

The "optics arrangement" is provided to provide e.g. guidance, deflection, focusing and reflection of the electromagnetic radiation, i.e. visible and/or invisible light.

In an example, the optics arrangement comprises an objective lens in vicinity to the sample receiving device The optics arrangement may further comprise a tube lens for focusing light from the sample to the sensor unit. A mirror can be provided to deflect the focused light towards the sensor unit to allow e.g. a compact arrangement.

The cylindrical lenses 32 modulate the radiation by focusing the radiation in one direction to a plurality of lines, e.g. parallel lines in case of parallel cylindrical lenses. The plurality of the first parts of intensified radiation and the plurality of the second parts of weak radiation are arranged in an alternating manner, as discussed above. In an example, as indicated in FIG. 2, the linear cylindrical lenses 32 are arranged adjacent to each other to provide a continuous modulation of the electromagnetic radiation from the source 20. The term "linear" relates to a linear extension of the lenses, as indicated in FIG. 3 showing a top view of the lens array 30.

In an example, indicated in FIG. 5, together with a further option, the radiation arrangement 12 comprises an illumination unit 40 with a light source 42. The lens array arrangement 28 comprises at least one illumination lens array 44 that is arranged between the light source 42 and the sample receiving device 14 and that modulates light from the light source such that an illumination distribution pattern is generated with a plurality of first parts of intensified illumination and a plurality of second parts of weak illumination. The illumination unit 40 could also comprise a condenser (not explicitly shown in FIG. 5), which is arranged between the illumination lens array 44 and the sample receiving device 14. The condenser works together with the illumination lens array 44 to form the desired illumination distribution pattern.

Instead of one, also two or more illumination lens arrays 44 are provided. According to an example, the optics arrangement 16 is configured for transmissive illumination mode for bright field mode scanning, in which light from the illumination unit 40 is transmitted through the sample being hold on the sample receiving device 14 and then directly towards the sensor unit 18.

In an example, the radiation arrangement 12 comprises only the illumination unit 40. The lens array is thus provided as the illumination lens array. It is noted that FIG. 5 shows also a further option, as described in the following.

According to another example, also shown as a further option in FIG. 5, however also provided without the above-mentioned option of the illumination unit 40, the radiation arrangement 12 comprises a fluorescence excitation unit 50 with an excitation light source 52 and an excitation filter 54 in front of the excitation light source 52. The lens array arrangement 28 comprises at least one excitation lens array 56 that is arranged between the excitation light source 52 and the sample receiving device 14 and that modulates excitation light from the excitation light source 52 such that an excitation distribution pattern is generated with a plurality of first parts of intensified excitation light and a plurality of second parts of weak excitation light.

Instead of one, also two or more excitation lens arrays 56 are provided.

As indicated above, in an example, the radiation arrangement 12 comprises only the fluorescence excitation unit 50. The lens array is thus provided as the excitation lens array. It is noted that FIG. 5 shows also a further option, as described above.

In an example, as indicated in FIG. 5, the radiation arrangement 12 comprises both the illumination unit 40 and the fluorescence excitation unit 50. The lens array arrangement thus comprises both the illumination lens array and the excitation lens array.

In an example, the optics arrangement 16 comprises a dichroic mirror 60 to allow a reflection of the excitation light towards the sample and to allow a transmission of light emanating from the sample towards the sensor unit 18.

In an example, the excitation lens array 56 is provided with lenses having a different focal length than the lenses of the illumination lens array 44.

In an example, the excitation lens array is arranged between the excitation light source 52 and the excitation filter 54, i.e. in front of (i.e. following, in terms of excitation light radiation direction or propagation) the excitation light source 52, but before (in terms of the excitation light radiation direction) of the excitation filter 54. In another example, the excitation lens array 56 is arranged between the excitation filter 54 and the sample receiving device 14 (i.e. the slide), i.e. following (in terms of excitation light radiation direction) the excitation filter 54, e.g. between excitation filter 54 and further optics.

In an example, the optics arrangement is configured for a reflective illumination mode for fluorescence mode scanning, in which excitation light from the fluorescence excitation unit is transmitted towards the sample, and in which generated fluorescence radiation is then collected and transmitted by the optics arrangement 16 towards the sensor unit, wherein the excitation light illuminated on the sample and the generated fluorescence radiation collected from the illuminated sample are at the same side of the sample receiving device 16.

In FIG. 5, as an option a further mirror 62 is provided that reflects the radiation towards the sensor unit 18. As a further option, FIG. 5 also shows the provision of an objective lens 64 arranged in vicinity to the sample receiving device 14.

In FIG. 6, an illustration of an object space 66 is indicated showing a respective radiation distribution pattern 68 with the intensified radiation parts 70 and the weak radiation parts 72.

FIG. 7 illustrates a top or front view of a sensor 74 being part of the sensor unit 18 according to an example. The sensor 74 is provided with a sensor pattern of a plurality of first parts of linear photo-active areas 76 and a plurality of second parts of photo-inactive areas 78 in between. The photo-active areas 76 can also be referred to as (linear) sensor segments, since these segments provide the sensing effect of the sensor unit 18. The photo-inactive areas 78 can also be referred to as segments, or non-active segments, since these segments do not contribute to the sensing effect. Instead of areas or segments, also the terms portions or parts can be used.

Dots 75 indicate that more or less lines of photo-active areas 76 can be provided. An empty part 77 indicates that the photo-active areas 76 may have a further or shorter extension in the linear direction. Hence, the sensor can vary in size and also in proportion.

The photo-active areas 76 comprise a plurality of sensor elements 80 arranged as (sensor) pixel lines. Hence, the sensor elements 80 can also be referred to as pixels. The sensor pattern thus provides an image space, i.e. an area across which image data can be measured, i.e. detected by the (sensor) pixel lines. One photo-active area 76 could comprise one or multiple pixel lines, for example, one photo-active area comprises four pixel lines. These pixel lines of a photo-active area work in time delay and integration mode (TDI mode), also referred to as time delay and integration scanning which can enhance sensitivity.

According to an example, the number of the plurality of linear cylindrical lenses of the at least one lens array matches the number of the plurality of linear photo-active areas of the sensor.

The image space thus corresponds to the object space that is defining a scanning area size of the sample. The object space is an area provided by the sample receiving device, across which image data can be detected during the scan.

The modulation of the light (in illumination mode, e.g. bright field mode, and/or in fluorescence mode) in the object space corresponds to the sensor or pixel line arrangement in the image space of the sensor unit 18.

The provision of the lens array arrangement 28 to modulate the radiation to provide the radiation distribution pattern in the object plane in combination with the linear photo-active areas arranged in form of the sensor pattern provides the use of a maximum amount of the light from the radiation arrangement, i.e. a maximum use of the output from the light source. Theoretically (or virtually) 100% of the light is used for scanning purposes.

The lens array arrangement with the cylindrical lenses 32 is thus provided to tailor the light distribution in the object plane and also in the imaging plane such that the light distribution matches the pixel line distribution of the sensor (also referred to as camera or camera unit).

The focal power of the cylindrical lenses needs to comply with the system distances of the (digital pathology) scanner and the condenser design (of the digital pathology scanner acting as a microscope). For example, an area of the object space of 1 μm (micrometer) by 1 μm relates to 4 by 4 pixels. In another example, an object space of 1025 μm by 540 μm relates to 4096 by 2160 pixels.

In an example, the number of lenses in the array corresponds to the number of the linear photo-active areas in the detector. As an example, the following formula can be used for approximating or determining the focal length of the individual cylindrical lens of the lens array arrangement:

$$\frac{\text{pupil entrance}}{f_{cyl}} = \frac{\text{object space width}}{f_{\mathit{eff}}}$$

wherein the pupil entrance is the entrance pupil of the condenser in bright field mode or the entrance pupil of the objective in fluorescence mode, $f_{cyl}$ is the focal length of the individual lenses in the array, $f_{\mathit{eff}}$ is the effective focal length of the condenser in bright field mode or of the objective in fluorescence mode, and "object space width" is the desired width to be obtained in the object space, for example it can be required to be larger than 540 μm (micrometer).

The formula depicts that different lens arrays are provided for bright field and fluorescence modes.

In an example, a regular repetitive pattern of the lenses is provided, i.e. with the same pitch. In another example, the pattern of the lenses is provided with an irregular pitch. In general, the pattern (and thus the pitch) relates to a pattern of sensitive areas of the sensor unit.

As an example, the sensor pattern is provided with a ratio of the photo-active areas to the photo-inactive areas of approximately smaller than 1:1. In an example, the ratio of the photo-active areas to the photo-inactive areas is 4:13. In other examples, other ratios are provided, such as smaller than 1:2, or smaller than 1:3 or smaller than 1:4, or smaller than 1:5, or ratios with values in between.

Hence, in an example, the linear photo-active areas comprise four lines of pixels and the photo-inactive areas are provided as a non-sensing space corresponding to a width of thirteen lines of pixels.

In the example of the radiation arrangement comprising the illumination unit, the number of the plurality of linear cylindrical lenses of the illumination lens array matches the number of the plurality of linear photo-active areas.

In the example of the radiation arrangement comprising the fluorescence excitation unit, the number of the plurality of linear cylindrical lenses of the excitation lens array matches the number of the plurality of linear photo-active areas.

In the example of the radiation arrangement comprising the illumination unit and the fluorescence excitation unit, the numbers of the plurality of linear cylindrical lenses of the illumination lens array and of the excitation lens array both match with the number of the plurality of linear photo-active areas. Due to the provision of the lens array arrangement, efficient use of light can provide an improvement that can be used to, for example, shorten the total scan time, e.g. more light faster scan speed possible, or to relax the specifications of the illumination unit.

In addition to combinations of features belonging to an embodiment, also any combination between features relating to different embodiment is considered to be disclosed with this application. All features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A digital pathology scanner, comprising:
a radiation arrangement;

a sample receiving device;
an optics arrangement; and
a sensor unit;
wherein the radiation arrangement includes a source that provides electromagnetic radiation for radiating a sample received by the sample receiving device;
wherein the optics arrangement is arranged between the sample receiving device and the sensor unit;
wherein the sensor unit is configured to provide image data of the radiated sample;
wherein a lens array arrangement is provided including at least one lens array arranged between the source and the sample receiving device;
wherein the at least one lens array includes a plurality of linear cylindrical lenses that modulate the electromagnetic radiation from the source such that, in an object plane, a radiation distribution pattern is generated with a plurality of first parts of intensified radiation and a plurality of second parts of weak radiation;
wherein the intensified radiation parts, more radiation is provided than without the use of the lens array arrangement; and
wherein the sensor unit includes a sensor with a sensor pattern of a plurality of first parts of linear photo-active areas and a plurality of second parts of photo-inactive areas in between;
wherein the number of the plurality of linear cylindrical lenses matches the number of the plurality of linear photo-active areas.

2. Digital pathology scanner according to claim 1, wherein the linear cylindrical lenses are arranged adjacent to each other to provide a continuous modulation of the electromagnetic radiation from the source.

3. Digital pathology scanner according to claim 1,
wherein the electromagnetic radiation source includes an illumination unit with a light source; and
wherein the plurality of linear cylindrical lenses form an illumination lens array that is arranged between the light source and the sample receiving device and that modulates light from the light source such that an illumination distribution pattern is generated with a plurality of first parts of intensified illumination and a plurality of second parts of weak illumination.

4. Digital pathology scanner according to claim 3, wherein the optics arrangement is configured for transmissive illumination mode for bright field mode scanning, in which light from the illumination unit is transmitted through the sample received by the sample receiving device and then directly towards the sensor unit.

5. Digital pathology scanner according to claim 1,
wherein the electromagnetic radiation source includes a fluorescence excitation unit with an excitation light source and an excitation filter in front of the excitation light source; and
wherein the plurality of linear cylindrical lenses form an excitation lens array that is arranged between the excitation light source and the sample receiving device and that modulates excitation light from the excitation light source such that an excitation distribution pattern is generated with a plurality of first parts of intensified excitation light and a plurality of second parts of weak excitation light.

6. Digital pathology scanner according to claim 5,
wherein the optics arrangement is configured for a reflective illumination mode for fluorescence mode scanning, in which excitation light from the fluorescence excitation unit is transmitted towards the sample, and in which generated fluorescence radiation is then collected and transmitted by the optics arrangement towards the sensor unit; and
wherein the excitation light illuminated on the sample and the generated fluorescence radiation collected from the illuminated sample are at the same side of the sample receiving device.

7. Digital pathology scanner according to claim 1, wherein each linear photo-active area includes one or multiple pixel lines, and these pixel lines work in time delay and integration mode.

8. Digital pathology scanner according to claim 1, wherein the sensor pattern is provided with a ratio of the photo-active areas to the photo-inactive areas of smaller than 1:1.

9. Digital pathology scanner according to claim 8, wherein the ratio of the photo-active areas to the photo-inactive areas is 4:13.

10. Digital pathology scanner according to claim 1, wherein the radiation distribution pattern of the lens array arrangement in an object plane of the sample receiving device corresponds to the sensor pattern.

11. A digital pathology scanner, comprising:
a radiation arrangement;
a sample receiving device;
a lens array arrangement;
an optics arrangement; and
a sensor unit;
wherein the optics arrangement is arranged between the sample receiving device and the sensor unit;
wherein the sensor unit is configured to provide image data of the radiated sample;
wherein the radiation arrangement includes an illumination unit with a light source for illuminating a sample received by the sample receiving device;
wherein the lens array arrangement includes an illumination lens array that is arranged between the light source and the sample receiving device and that modulates light from the light source such that an illumination distribution pattern is generated with a plurality of first parts of intensified illumination and a plurality of second parts of weak illumination; and
wherein the optics arrangement is configured for transmissive illumination mode for bright field mode scanning, in which light from the illumination unit is transmitted through the sample received by the sample receiving device and then directly towards the sensor unit;
wherein the sensor unit includes a sensor with a sensor pattern of a plurality of first parts of linear photo-active areas and a plurality of second parts of photo-inactive areas in between; and
wherein the number of the plurality of linear cylindrical lenses matches the number of the plurality of linear photo-active areas.

12. Digital pathology scanner according to claim 11,
wherein the radiation arrangement includes a fluorescence excitation unit with an excitation light source and an excitation filter in front of the excitation light source for illuminating the sample received by the sample receiving device; and
wherein the lens array arrangement includes an excitation lens array that is arranged between the excitation light source and the sample receiving device and that modulates excitation light from the excitation light source such that an excitation distribution pattern is generated with a plurality of first parts of intensified excitation light and a plurality of second parts of weak excitation light;

wherein the optics arrangement is configured for a reflective illumination mode for fluorescence mode scanning, in which excitation light from the fluorescence excitation unit is transmitted towards the sample, and in which generated fluorescence radiation is then collected and transmitted by the optics arrangement towards the sensor unit; and wherein the excitation light illuminated on the sample and the generated fluorescence radiation collected from the illuminated sample are at the same side of the sample receiving device.

13. Digital pathology scanner according to claim 11, wherein each linear photo-active area includes one or multiple pixel lines, and these pixel lines work in time delay and integration mode.

14. Digital pathology scanner according to claim 11, wherein the illumination distribution pattern of the illumination lens array in an object plane of the sample receiving device corresponds to the sensor pattern.

15. A digital pathology scanner, comprising:
a radiation arrangement;
a sample receiving device;
a lens array arrangement;
an optics arrangement; and
a sensor unit;
wherein the optics arrangement is arranged between the sample receiving device and the sensor unit;
wherein the sensor unit is configured to provide image data of the radiated sample;
wherein the radiation arrangement includes an illumination unit with a light source for illuminating a sample received by the sample receiving device;
wherein the lens array arrangement includes an illumination lens array that is arranged between the light source and the sample receiving device and that modulates light from the light source such that an illumination distribution pattern is generated with a plurality of first parts of intensified illumination and a plurality of second parts of weak illumination;

wherein the radiation arrangement further includes a fluorescence excitation unit with an excitation light source and an excitation filter in front of the excitation light source for illuminating the sample received by the sample receiving device; and wherein the lens array arrangement further includes an excitation lens array that is arranged between the excitation light source and the sample receiving device and that modulates excitation light from the excitation light source such that an excitation distribution pattern is generated with a plurality of first parts of intensified excitation light and a plurality of second parts of weak excitation light;

wherein the sensor unit includes a sensor with a sensor pattern of a plurality of first parts of linear photo-active areas and a plurality of second parts of photo-inactive areas in between; and wherein the number of the plurality of linear cylindrical lenses matches the number of the plurality of linear photo-active areas.

16. Digital pathology scanner according to claim 15, wherein each linear photo-active area includes one or multiple pixel lines, and these pixel lines work in time delay and integration mode.

17. Digital pathology scanner according to claim 15, wherein at least one of:
the illumination distribution pattern of the illumination lens array in an object plane of the sampling receiving device corresponds to the sensor pattern; and
the excitation distribution pattern of the excitation lens array in the object plane of the sampling receiving device corresponds to the sensor pattern.

* * * * *